(12) United States Patent
Reimert

(10) Patent No.: US 10,878,798 B2
(45) Date of Patent: Dec. 29, 2020

(54) EARPHONE WITH AN ACTIVE NOISE CANCELLING FEEDBACK MICROPHONE ARRANGED AT THE REAR-SIDE OF A SPEAKER DIAPHRAGM

(71) Applicant: GN Audio A/S, Ballerup (DK)

(72) Inventor: Jacob Reimert, Ballerup (DK)

(73) Assignee: GN AUDIO A/S, Ballerup (DK)

( * ) Notice: Subject to any disclaimer, the term of this patent is extended or adjusted under 35 U.S.C. 154(b) by 0 days.

(21) Appl. No.: 16/705,141

(22) Filed: Dec. 5, 2019

(65) Prior Publication Data
US 2020/0184945 A1 Jun. 11, 2020

(30) Foreign Application Priority Data

Dec. 7, 2018 (EP) ..................................... 18211010

(51) Int. Cl.
*G10K 11/178* (2006.01)
*H04R 1/10* (2006.01)
(Continued)

(52) U.S. Cl.
CPC ..... *G10K 11/17875* (2018.01); *H04R 1/1008* (2013.01); *H04R 1/1041* (2013.01);
(Continued)

(58) Field of Classification Search
CPC ......... G10K 11/17875; G10K 11/1788; G10K 11/178; G10K 11/1784; G10K 2210/1081;
(Continued)

(56) References Cited

U.S. PATENT DOCUMENTS 5,909,498 A * 6/1999 Smith ................... H04R 1/1016
381/375
7,466,838 B1 * 12/2008 Moseley .............. G10K 11/178
381/370
(Continued)

FOREIGN PATENT DOCUMENTS

| EP | 0195641 | 9/1986 |
|---|---|---|
| GB | 1530814 | 11/1978 |
| WO | 2006128768 | 12/2006 |

OTHER PUBLICATIONS

Extended European Search Report for European patent application No. 18211010.6 dated May 9, 2019.

*Primary Examiner* — Ahmad F. Matar
*Assistant Examiner* — Sabrina Diaz
(74) *Attorney, Agent, or Firm* — Hamre, Schumann, Mueller & Larson, P.C.

(57) ABSTRACT

An earphone (1) comprising an earphone housing (2), a speaker unit (3), the speaker unit (3) comprising a diaphragm (4). A front chamber (29) is defined in the earphone between a front side (31) of the diaphragm (4) and the user (7), when the earphone (1) is worn. A rear chamber (27) is defined between the earphone housing (2) and a rear side (32) of the diaphragm (4). The earphone (1) comprises an active noise cancelling feedback microphone (9), which is arranged in the rear chamber (27) and which comprises a microphone opening (11). The diaphragm (4) comprises a cylindrical part (14), to which a voice coil (12) is attached, and an outer ring part (15) extending from the cylindrical part (14) in a direction away from a centre axis (30) of the diaphragm (4). The feedback microphone (9) is arranged farther from the centre axis (30) than the voice coil (12).

8 Claims, 4 Drawing Sheets

(51) Int. Cl.
*H04R 9/02* (2006.01)
*H04R 9/06* (2006.01)

(52) U.S. Cl.
CPC .............. *H04R 9/025* (2013.01); *H04R 9/06* (2013.01); *G10K 2210/1081* (2013.01); *G10K 2210/3011* (2013.01); *G10K 2210/3026* (2013.01); *H04R 2460/01* (2013.01)

(58) Field of Classification Search
CPC ... G10K 2210/3011; G10K 2210/3026; G10K 2210/108; H04R 1/1008; H04R 1/1041; H04R 1/1083; H04R 5/033; H04R 9/025; H04R 9/06; H04R 2460/01
USPC ........................................ 381/71.6, 71.1, 94.1
See application file for complete search history.

(56) References Cited

U.S. PATENT DOCUMENTS

| | | | | |
|---|---|---|---|---|
| 7,499,555 | B1* | 3/2009 | Isvan | H04R 1/1075 |
| | | | | 381/182 |
| 8,077,874 | B2* | 12/2011 | Sapiejewski | H04R 1/1075 |
| | | | | 381/74 |
| 9,613,614 | B2* | 4/2017 | Huang | G10K 11/17857 |
| 2011/0286607 | A1* | 11/2011 | Kimura | G10K 11/17857 |
| | | | | 381/71.6 |
| 2014/0169579 | A1* | 6/2014 | Azmi | G10K 11/16 |
| | | | | 381/71.6 |
| 2014/0294182 | A1* | 10/2014 | Axelsson | H04R 1/1083 |
| | | | | 381/56 |
| 2016/0314779 | A1 | 10/2016 | Huang | |
| 2019/0156814 | A1* | 5/2019 | Eguchi | G10K 11/17823 |
| 2019/0191237 | A1* | 6/2019 | Wang | G10K 11/17857 |

\* cited by examiner

EARPHONE WITH AN ACTIVE NOISE CANCELLING FEEDBACK MICROPHONE ARRANGED AT THE REAR-SIDE OF A SPEAKER DIAPHRAGM

TECHNICAL FIELD

The invention relates an earphone comprising an earphone housing, a speaker unit, the speaker unit comprising a diaphragm, wherein a front chamber is defined in the earphone between a front side of the diaphragm and the user, when the earphone is worn, and wherein a rear chamber is defined between the earphone housing and a rear side of the diaphragm, and wherein the earphone comprises an active noise cancelling feedback microphone, which is arranged in the rear chamber, and which comprises a microphone opening, the diaphragm comprises a cylindrical part, to which the voice coil is attached, and an outer ring part extending form the cylindrical part in a direction away from a centre axis of the diaphragm. The invention also relates to a method of manufacturing of an earphone comprising an active noise cancelling feedback microphone.

BACKGROUND ART

Headsets and headphones can be adapted to reduce the amount of ambient noise, that reaches the users ear. This noise reduction can be done by passive means or active means. Passive means are simply mechanical isolation of the ear from the surroundings, such as a circumaural earphone housing with isolated walls that prevents ambient noise to reach the ear. Headphones with active noise cancellation are called ANC headphones. They comprise an electronic circuit that generates a sound signal that corresponds to the ambient noise but is inverted, which means phase changed 180 degrees. The active noise cancellation reduces the noise experienced by the user in the lower frequency bands. The passive reduction means reduces the experienced noise in the higher frequency bands. There are two types of acoustic noise cancellation. Feed forward noise cancellation and feedback noise cancellation. Often a combination of both are used. In feed forward noise cancellation systems, a noise capturing microphone captures noise outside the earphone and sends a signal to the noise cancellation system which inverts the signal before it is added to the audio signal forwarded to the earphone speaker. In feedback noise cancellation systems, a noise feedback microphone is provided between the headphone speaker and the eardrum. The captured audio is fed back to the noise cancellation system. This specification relates to earphones provided with a feedback noise cancellation system. A challenge in feedback ANC systems is to place the microphone as close to the speaker diaphragm as possible. The smaller distance the smaller is the phase shift/delay. If the phase shift is small, it is possible to provide noise cancellation in higher frequencies.

EP 0 195 641 B1 and WO 2006/128768 disclose earphones where an ANC feedback microphone is arranged on the rear side of the speaker's diaphragm within the diameter of the voice coil.

There is a need for alternative positions of an ANC feedback microphone.

DISCLOSURE OF INVENTION

An earphone according to the invention is characterised in, that the feedback microphone is arranged farther from the centre axis than the voice coil. In many cases, such an arrangement is advantageous. F. ex. if there the circumference of the voice coil is small and/or the magnetic circuit, which the voice coil is a part of, should be as efficient as possible leaving only little space for a microphone and wires.

The distance between the microphone opening and rear side the diaphragm can be less than 5 mm. With such a solution, the ANC system can be efficient and provide active noise cancelling at relatively high frequencies due to low phase shift, while the microphone is arranged in a protected manner "behind" the diaphragm.

According to an embodiment, the distance between the microphone opening and the rear side of the diaphragm is less than 4 mm, less than 3 mm, less than 2 mm, or less than 1 mm. The microphone unit must not touch the diaphragm, so the distance must be greater than the diaphragm's movement in the direction of the microphone unit during sound generation. As smaller membranes normally have smaller movements, the distance can normally be chosen smaller with small diaphragms. As the position of the microphone unit according to this invention is behind the diaphragm, it is easier to arrange it close to the rear side of the diaphragm, as it will not so easily be inadvertently displaced by external forces.

According to an embodiment, the speaker unit further comprising a through-going hole extending parallel with a centre axis of the voice coil and within the circumference of the voice coil, wherein the feedback microphone unit is mounted in the through-going hole. The hole may fulfil two purposes: To provide positioning of the ANC feedback microphone and the provide a vent to the reaming rear chamber.

According to an embodiment, the magnet is a ring-shaped magnet, and the magnetic circuit unit comprises an outer pole piece and an inner pole piece, wherein the magnetic gap is provided between the outer pole piece and the inner pole piece, and wherein the through-going hole is provided in the inner pole piece.

According to an embodiment, the feedback microphone is arranged between the voice coil and the centre axis of the voice coil.

According to an embodiment, the microphone opening is within a distance of 2 mm from the cylindrical part of the diaphragm.

According to an embodiment, the feedback microphone is a MEMS-type microphone. MEMS refer to Microelectromechanical systems.

According to an embodiment, the feedback microphone is arranged on a "Flex PCB" (flexible printed circuit board).

According to an embodiment, the diaphragm covers the area encircled by the voice coil.

BRIEF DESCRIPTION OF THE DRAWINGS

The invention is explained in detail below with reference to the drawings, in which.

MODES FOR CARRYING OUT THE INVENTION

Figure 1:
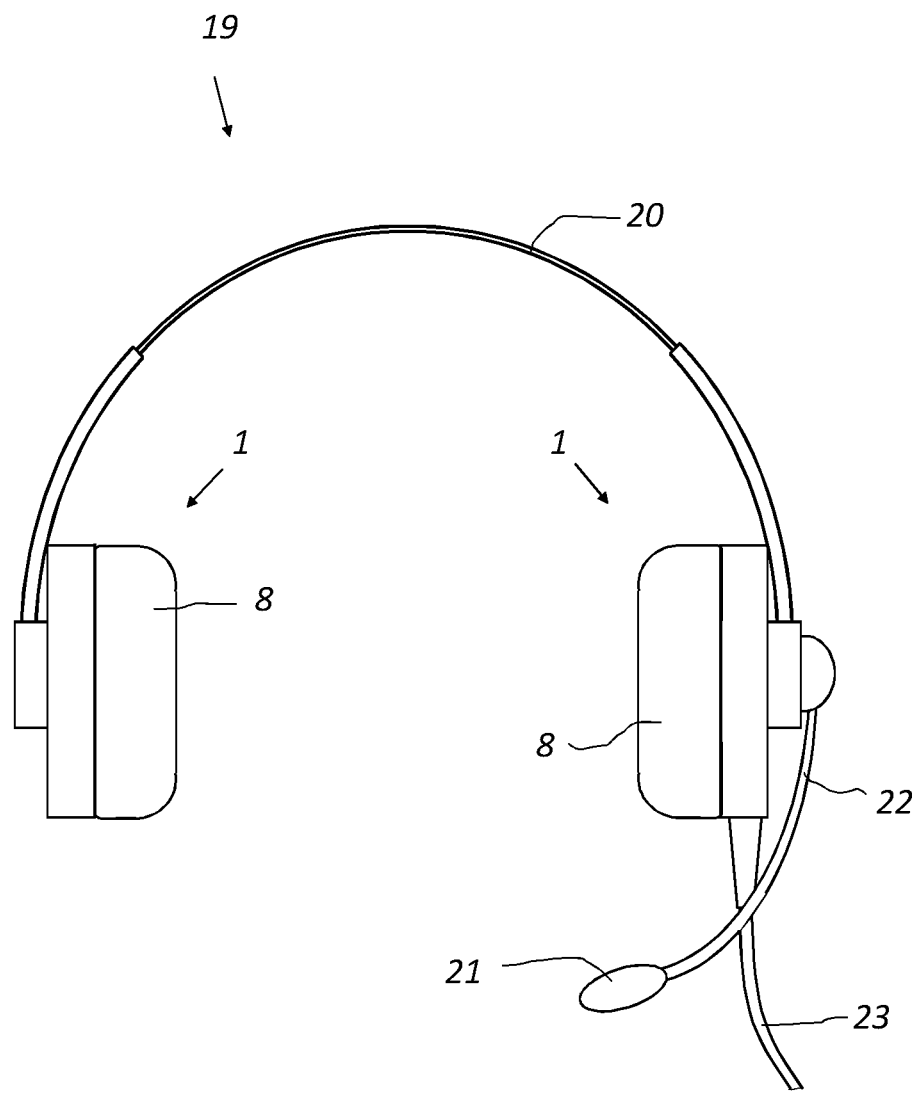
FIG. 1 is a schematic view of a corded headset comprising two earphones.

FIG. 1 discloses a corded headset 19 comprising first and second earphones 1, 1, each comprising an ear cushion 8. The earphones 1 are interconnected by an adjustable headband 20. A microphone arm 22 with a microphone 21 at the distal end extends from one of the earphones 1 and a cord 23 extends from the same earphone 1 and connects it to f. ex. a personal computer.

Figure 2:
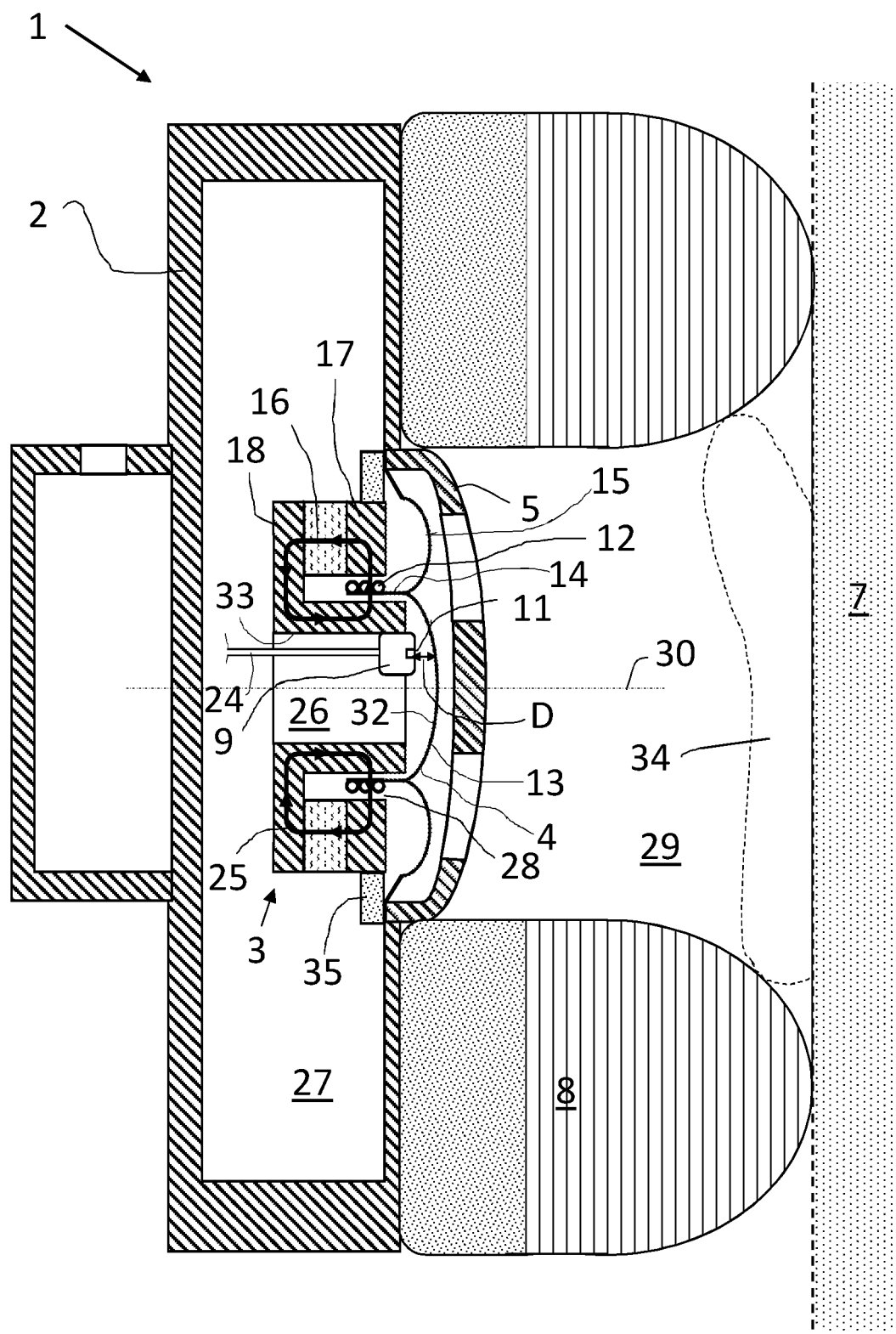
FIG. 2 is a cross-sectional view through an earphone of a headset with a feedback ANC microphone according to a first embodiment.

FIG. 2 is a cross-sectional view through one of the earphones of a feedback ANC headset according to a first embodiment of the invention. The earphone 1 comprises an earphone housing 2, a speaker unit 3 and an ear cushion 8. At the front, of the speaker unit comprises a protection device 5 with sound apertures 10. When the headset is worn by a user as shown schematically on FIG. 2, where the users head is having the reference number 7 and the users ear the reference number 34, a front chamber 29 is defined by the speaker unit 3, the ear cushion 8 and the user's head 7. The speaker unit 3 comprises a ring-shaped plate member 35, a diaphragm 4 with a central dome part 13, an outer ring part 15, a cylindrical part 14 and a voice coil 12 attached to the cylindrical part 14. The voice coil 12 is placed in a magnetic gap 28 of a magnetic circuit 25. The magnetic circuit 25 comprises a ring-shaped magnet 16, an inner pole piece 18 and an outer pole piece 17, also called a yoke. The magnetic gap 28 is arranged between the outer pole piece 17 and the inner pole piece 18. The outer side of the outer piece 17, the ring-shaped plate member 35 and the housing 2 defines a rear chamber 27. The protection device 5 protects the diaphragm 4 from being damaged by f. ex. a user's finger during handling of the headset 19. The protection device 5 often carries a feedback ANC microphone 9 of conventional feedback ANC earphones. The speaker unit 3 in general, the diaphragm 4 and the voice coil 12 are all circular in relation to a centre axis 30. The inner polepiece 18 comprises a through-going hole 26, which serves two purposes. It provides a vent between the rear side of the diaphragm 4 and the remaining rear chamber 27 and provides a seat for a feedback ANC microphone unit 9. The feedback microphone unit 9 is attached to the inner wall 33 of the through-going hole 26 close to the rear side 32 of the diaphragm 4. A microphone opening 11 of the feedback microphone unit 9 faces the rear side 32 of the diaphragm. The distance D between the microphone opening 11 and the rear side 32 of the diaphragm 4 is about 2 mm. The smaller the distance D is the better, as a smaller phase shift between the audio generated by the diaphragm 4 and the audio sensed by the microphone unit 9 is obtained. As the problems with phase shift or phase delay grows with the frequency, a small distance D means, that noise cancelling can be carried out at a higher frequency. A wire 24 connects the feedback microphone unit 9 to the not shown ANC circuit. It can be an advantage to provide the microphone opening 11 close to the voice coil 12, as there also is a phase shift across the diaphragm 4. Thus, a microphone opening 9 arranged at the centre axis 30 would be longer from the voice coil than shown in FIG. 2. A big advantage of the microphone unit 9 being arranged in the through-going hole 26 is also, that it is well protected. A user cannot reach and displace or destroy the microphone unit. An embodiment has the following dimensions: Diameter of diaphragm: 36 mm, diameter of through-going bore: 10 m, length of through going bore: 6 mm, diameter of cylindrical part/voice coil 14 mm, distance D between microphone opening 11 and rear side of diaphragm: 2 mm.

Figure 3:
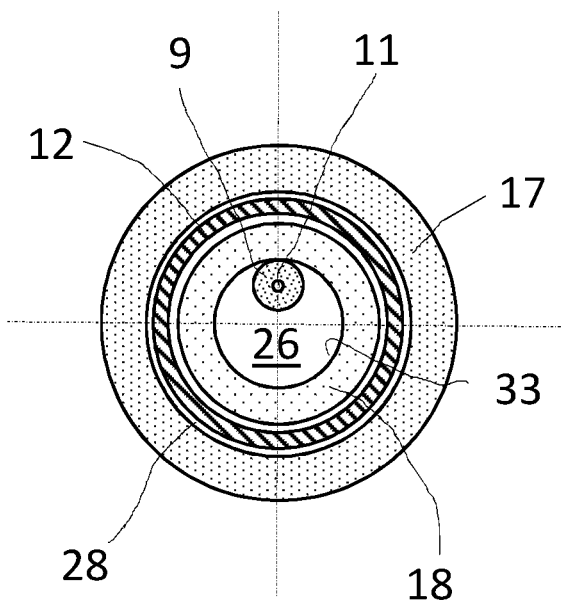
FIG. 3 is a schematic front view of the magnetic circuit unit.

FIG. 3 is a schematic front view of the magnetic circuit unit 3. The voice coil 12 is arranged in the narrow magnetic gap 28 between the outer pole piece 17 and the inner pole piece 18. The microphone unit 9 is arranged at an inner wall 33 of the through-going hole 26.

Figure 4:
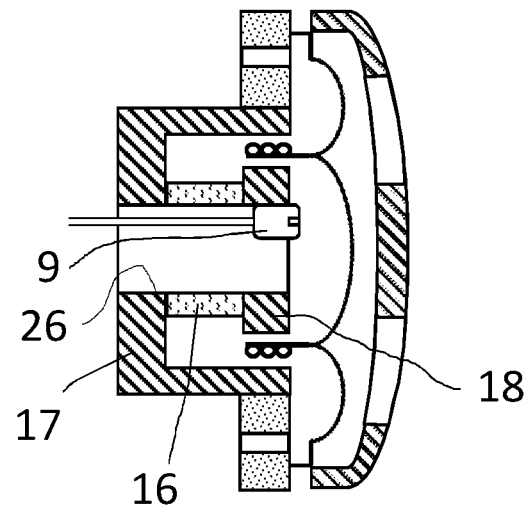
FIG. 4 is a cross-sectional view through a speaker unit according to a second embodiment.

FIG. 4 is a cross-sectional view through a speaker unit 3 according to a second embodiment. The outer pole piece 17 and the inner pole piece 18 are dimensioned different and the ring-shaped magnet 16 is arranged within the periphery of the voice coil 12.

Figure 5:
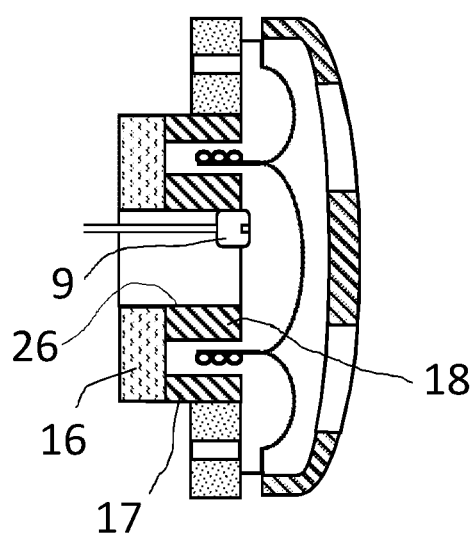
FIG. 5 is a cross-sectional view through a speaker unit according to a third embodiment of the invention.

FIG. 5 is a cross-sectional view through a speaker unit 3 according to a third embodiment. Here the ring-shaped magnet 16 is arranged at the bottom of the speaker unit 3.

Figure 6:
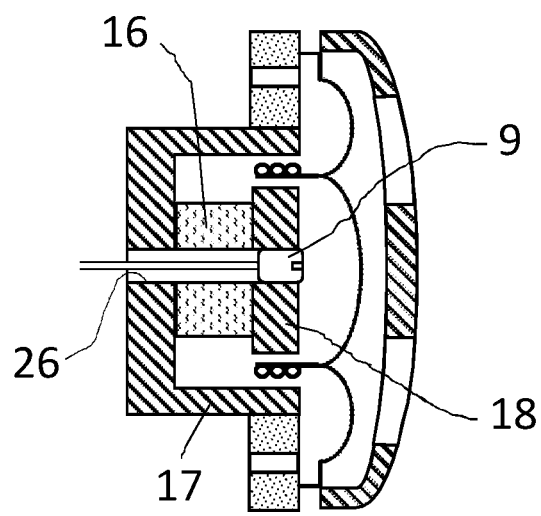
FIG. 6 is a cross-sectional view through a speaker unit according to a fourth embodiment.

FIG. 6 is a cross-sectional view through a speaker unit 3 according to a fourth embodiment. The microphone unit 9 fills out the through-going hole 26.

Figure 7:
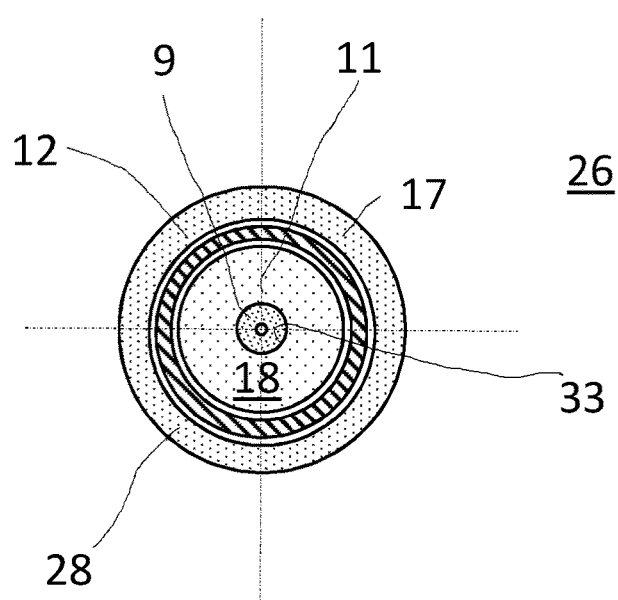
FIG. 7 is a front view of the magnetic circuit of the driver unit shown in FIG. 6.

FIG. 7 shows a front view of the magnetic circuit of the driver unit 3 shown in FIG. 6.

Figure 8:
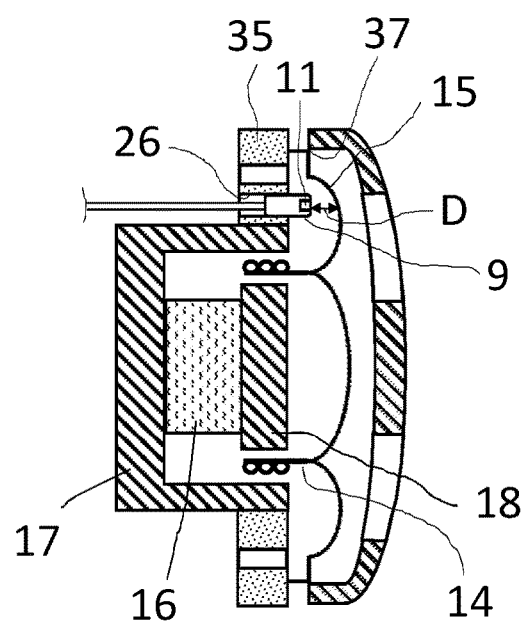
FIG. 8 is across-sectional view through a fifth embodiment of the invention.

FIG. 8 shows a cross-sectional view through a fifth embodiment. Here the microphone 9 is arranged in a through-going hole 26 in the ring-shaped plate member 35 of driver unit. Thus, the microphone opening 11 faces the rear side 32 of the cylindrical part 15 of diaphragm 5.

Figure 9:
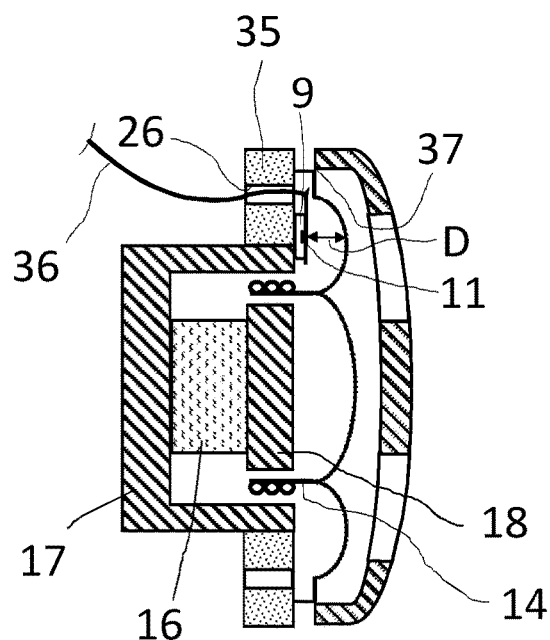
FIG. 9 is a cross-sectional view through a sixth embodiment.

FIG. 9 shows a cross-sectional view through a sixth embodiment. Here the microphone 9 is embodied as a so-called MEMS-type microphone, which is mounted on a band of flex PCB 36, which is passed through a through-going hole 26 in the ring-shaped plate member 35 of driver unit 3. The microphone 9 is adhered the plate member 35 and the outer pole piece 17. The microphone is a so-called "bottom-port microphone", which has its microphone opening 11 on the same side as its PCB mounting pads. A hole is therefore provided in the flex PCB 36 at the position of the microphone opening 11. Thus, the microphone opening 11 faces the rear side 32 of the ring part 15 of diaphragm 4.

Figure 10:
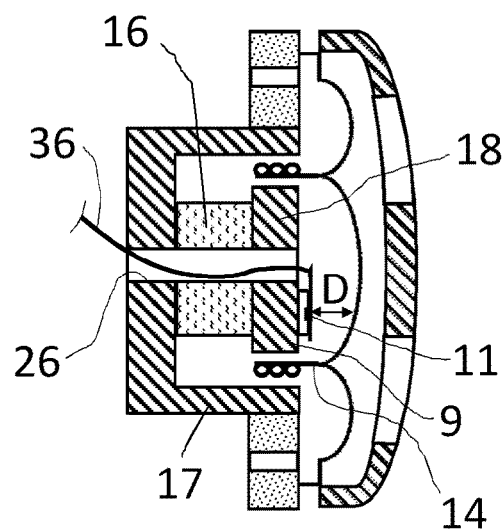
FIG. 10 is a cross-sectional view through a seventh embodiment.

FIG. 10 shows a cross-sectional view through an eighth embodiment. Like in FIG. 9, the microphone is a MEMS-type microphone 9 arranged on a band of flex PCB 36. In this case, the microphone 9 is attached to the surface of the inner pole piece 18, and the flex PCB is passed through a through-going hole 26 of the magnetic circuit unit 25.

In the embodiments shown in FIGS. 9 and 10, the microphone opening 11 is arranged relatively close to the voice coil 12. This an advantage, as phase shift occurs across the diaphragm, whereby the phase shift is lower, the closer the microphone opening 11 is to the voice coil 12. It is and advantage to keep the In all the discloses embodiments, the microphone opening 11 is arranged within a short distance from the rear side 32 of the diaphragm 4. Here it is well-protected and provides the possibility of an efficient active noise feedback system.

In the shown embodiments, the voice coil, the cylindrical part and the diaphragm are circular. However, they could have other shapes and be f. ex. rectangular or quadratic when seen I the direction of the centre axis.

REFERENCE SIGNS

D distance between microphone opening and diaphragm
1 earphone
2 earphone housing
3 speaker unit
4 diaphragm
5 protecting device
6 microphone channel
7 user's head
8 ear cushion
9 microphone unit
10 sound aperture
11 microphone opening
12 voice coil
13 dome part of diaphragm
14 cylindrical part of diaphragm
15 ring part of diaphragm
16 magnet
17 outer pole piece
18 inner pole piece/yoke
19 headset
20 headband
21 voice microphone
22 microphone arm
23 headset cable
24 microphone wiring
25 magnetic circuit unit
26 through-going hole
27 rear chamber
28 magnetic gap
29 front chamber
30 centre axis
31 front side of the diaphragm
32 rear side of the diaphragm
33 Inner wall of through-going hole
34 ear
35 ring-shaped plate member of driver unit
36 flex PCB
37 outer diameter of cylindrical part of diaphragm

The invention claimed is:

1. An earphone comprising an earphone housing, a speaker unit, the speaker unit comprising a diaphragm, wherein a front chamber is defined in the earphone between a front side of the diaphragm and a user, when the earphone is worn, and wherein a rear chamber is defined between the earphone housing and a rear side of the diaphragm, and wherein the earphone comprises an active noise cancelling feedback microphone, which is arranged in the rear chamber facing the rear side of the diaphragm, and which comprises a microphone opening, wherein the diaphragm comprises a cylindrical part, to which a voice coil is attached, and an outer ring part extending from the cylindrical part in a direction away from a centre axis of the diaphragm, wherein the feedback microphone is arranged farther from the centre axis than the voice coil.

2. An earphone according to claim 1, wherein a distance between the microphone opening and the rear side of the diaphragm is less than 5 mm.

3. An earphone according to claim 2, wherein the distance between the microphone opening and the rear side of the diaphragm is less than 4 mm, less than 3 mm, less than 2 mm, or less than 1 mm.

4. An earphone according to claim 3, wherein the speaker unit further comprises a magnetic circuit unit comprising a magnet, magnetic pole pieces, and a gap, in which the voice coil is received.

5. An earphone according to claim 1, wherein the feedback microphone is arranged on a flex PCB.

6. An earphone according to claim 5, wherein the microphone opening is within a distance of 2 mm from the cylindrical part of the diaphragm.

7. An earphone according to claim 6, wherein the feedback microphone is a MEMS-type microphone.

8. An earphone according to claim 5, wherein the diaphragm covers the area encircled by the voice coil.

* * * * *